US009933073B2

(12) United States Patent
Goto et al.

(10) Patent No.: US 9,933,073 B2
(45) Date of Patent: Apr. 3, 2018

(54) AIRCRAFT

(71) Applicant: MITSUBISHI AIRCRAFT CORPORATION, Aichi (JP)

(72) Inventors: Shingo Goto, Aichi (JP); Toshiaki Sugimura, Aichi (JP)

(73) Assignee: MITSUBISHI AIRCRAFT CORPORATION, Aichi (JP)

( * ) Notice: Subject to any disclaimer, the term of this patent is extended or adjusted under 35 U.S.C. 154(b) by 275 days.

(21) Appl. No.: 14/637,561

(22) Filed: Mar. 4, 2015

(65) Prior Publication Data

US 2016/0040782 A1 Feb. 11, 2016

(30) Foreign Application Priority Data

Aug. 8, 2014 (JP) .................................. 2014-162163

(51) Int. Cl.
| | |
|---|---|
| *F16J 15/02* | (2006.01) |
| *B64D 15/20* | (2006.01) |
| *B64C 1/14* | (2006.01) |
| *B61D 49/00* | (2006.01) |
| *G01N 19/10* | (2006.01) |

(52) U.S. Cl.
CPC .............. *F16J 15/02* (2013.01); *B61D 49/00* (2013.01); *B64C 1/14* (2013.01); *B64D 15/20* (2013.01); *F16J 15/021* (2013.01); *G01N 19/10* (2013.01)

(58) Field of Classification Search
CPC .................................. B64C 1/14; B64D 15/20
See application file for complete search history.

(56) References Cited

U.S. PATENT DOCUMENTS

| | | | | | |
|---|---|---|---|---|---|
| 4,388,502 | A | * | 6/1983 | Cohn ...................... | B64C 21/10 367/906 |
| 7,690,598 | B1 | * | 4/2010 | Plattner .................. | B64D 13/02 244/129.1 |

FOREIGN PATENT DOCUMENTS

| | | |
|---|---|---|
| JP | 2007-521463 A | 8/2007 |
| WO | 2005/020175 A1 | 3/2005 |

OTHER PUBLICATIONS

Anthony, Sebastian, "Japanese maglev train begins public testing, buzzes peaceful countryside at 313 mph", Extreme Tech, Aug. 30, 2013, https://www.extremetech.com/extreme/165372-japanese-maglev-train-begins-public-testing-buzzes-peaceful-countryside-at-313-mph.*

* cited by examiner

*Primary Examiner* — Paul West
(74) *Attorney, Agent, or Firm* — Pearne & Gordon LLP

(57) ABSTRACT

An aircraft including: a penetration member that penetrates an airframe between an inside and an outside via an opening provided in the airframe; a seal that seals a gap set between an opening formation member forming the opening and the penetration member; and a retainer that presses the seal against the penetration member and the opening formation member, wherein each of the penetration member and the opening formation member includes a receiving section that receives the seal, both of the receiving sections are arranged along a direction connecting one side and the other side of the gap with the gap therebetween, and the seal is fixed to only one of the receiving section of the penetration member and the receiving section of the opening formation member.

20 Claims, 13 Drawing Sheets

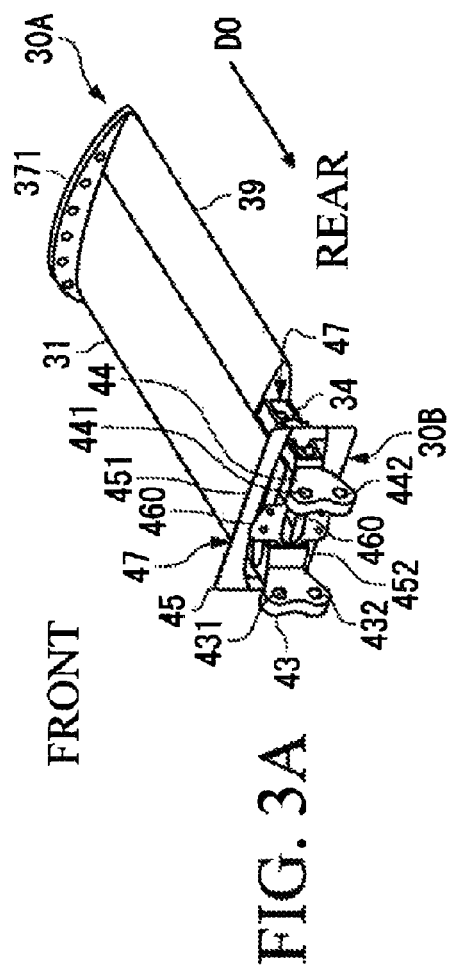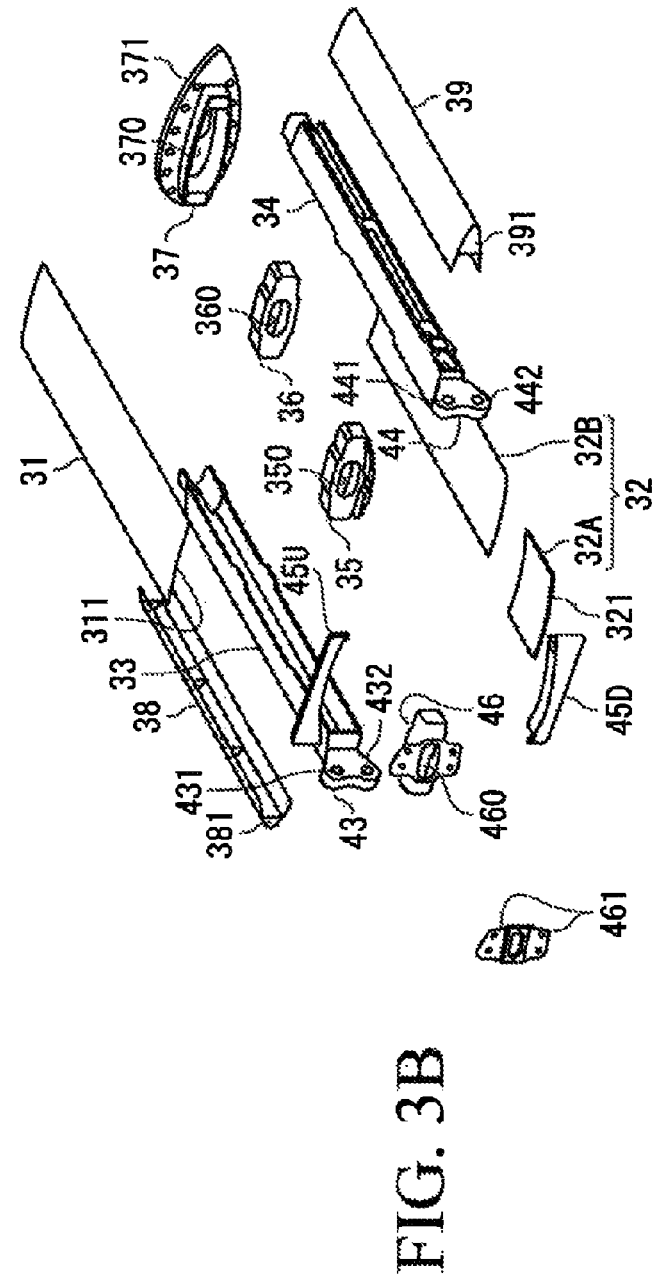

AIRCRAFT

BACKGROUND OF THE INVENTION

Field of the Invention

The present invention relates to an aircraft having a structure for ensuring airtightness.

Description of the Related Art

A measuring device that measures a moisture content in the atmosphere is used for obtaining icing conditions on an airframe in a test flight of aircraft (JP2007-521463A).

The measuring device can be installed outside the airframe by fixing the measuring device to an arm that is provided on the airframe and extends out of the airframe.

In order to provide the arm to which the measuring device is fixed on the airframe, it is necessary for a member prepared in the airframe to receive an aerodynamic load applied to the measuring device and the arm during a flight. Since the aerodynamic load cannot be received only by a skin (an outer plate), it is difficult to achieve a configuration in which a proximal end of the arm is supported only on an outer surface side of the airframe without passing the arm through the airframe. Thus, the arm is required to penetrate the airframe to be coupled to a member that is prepared on an airframe inner side and can receive the aerodynamic load.

When the arm penetrates the airframe, it is necessary to ensure airtightness between the arm and the airframe in order to hold pressurization inside the airframe. Therefore, a gap between the arm and the airframe is sealed by a seal member, and the seal member is fixed to a receiving member.

When the aerodynamic load is applied to the arm during a flight, the arm is deformed. Since the arm penetrates the airframe, a load generated by the deformation of the arm is input to the airframe from the arm. It is necessary to prevent the airframe from being thereby damaged, or the seal member from being thereby displaced to impair the airtightness.

An object of the present invention is to provide an aircraft having an airtight structure capable of reliably holding airtightness inside an airframe even when a member penetrating the airframe between the inside and the outside is deformed by an aerodynamic load.

SUMMARY OF THE INVENTION

An aircraft according to the present invention includes: a penetration member that penetrates an airframe between an inside and an outside via an opening provided in the airframe; a seal that seals a gap set between an opening formation member forming the opening and the penetration member; and a retainer that presses the seal against the penetration member and the opening formation member, wherein each of the penetration member and the opening formation member includes a receiving section that receives the seal, both of the receiving sections are arranged along a direction connecting one side and the other side of the gap with the gap therebetween, and the seal is fixed to only one of the receiving section of the penetration member and the receiving section of the opening formation member.

The "opening" in the present invention includes all types of openings provided in the airframe, including an opening of a window or a door itself previously prepared in the airframe for various purposes, an opening prepared in a substitute member capable of replacing a panel member for closing the above opening, and an opening formed by modifying the airframe in order to pass the penetration member through the airframe.

Also, the "opening" brings the inside and the outside of the airframe into communication with each other. The penetration member penetrates the airframe between the inside and the outside via the opening.

In the present invention, the seal is fixed to only one of the penetration member and the opening formation member, and is simply supported by the other so as to be displaceable.

Therefore, when the penetration member is deformed by an aerodynamic load to cause relative displacement of the penetration member and the opening formation member, the seal slides to be displaced on the side where the seal is simply supported. Accordingly, a load can be prevented from being directly input to the opening formation member from the penetration member, and airtightness between the penetration member and the opening formation member can be held.

In the aircraft of the present invention, the opening through which the penetration member is passed may be formed in a window substitute member that replaces a window panel (an original window panel) originally provided in a window frame of a window provided in the airframe. The window substitute member corresponds to the opening formation member. In this case, the opening of the window substitute member is arranged in an opening of the window frame, and the penetration member penetrates the airframe via both the opening of the window frame and the opening of the window substitute member.

In the aircraft of the present invention, the opening formation member may include a support that rises from a peripheral edge portion of the formed opening toward an airframe inner side along a penetration direction in which the penetration member penetrates the airframe, and a flange as the receiving section that is provided on the support, and the flange and the receiving section of the penetration member may be arranged along a direction perpendicular to or substantially perpendicular to the penetration direction with the gap therebetween.

When the support is provided on the opening formation member as described above, the receiving section can be easily provided on the opening formation member as the flange of the support along the direction perpendicular to or substantially perpendicular to the penetration direction. By sliding the seal along the flange, it is possible to prevent load input from the penetration member to the opening formation member or the airframe.

In the aircraft of the present invention, the opening formation member may include a peripheral wall that rises from a peripheral edge portion of the formed opening toward an airframe inner side along a penetration direction in which the penetration member penetrates the airframe, the penetration member may include an annular portion that is arranged with the gap between the annular portion and a distal end of the peripheral wall, and an outer peripheral portion of the peripheral wall as the receiving section of the opening formation member and an outer peripheral portion of the annular portion as the receiving section of the penetration member may be arranged along the penetration direction.

The penetration member in the present invention may include a first portion that is located outside the airframe, and a second portion that is located inside the airframe, and a detection device that detects a physical quantity may be provided at the first portion.

The penetration member in the present invention may also include a detection device that detects a physical quantity outside the airframe, and a member that is integrated with the device.

Moreover, the penetration member in the present invention may be configured as a portion of a detection device that detects a physical quantity outside the airframe.

The detection device in the present invention may detect a physical quantity with regard to a water droplet included in an atmosphere outside the airframe.

The detection device can be used for obtaining icing conditions on the airframe.

The detection device in the present invention may also detect at least a total pressure out of the total pressure and a static pressure. The detection device may include a pitot tube. The total pressure corresponds to a pressure of air pushed in from a front opening of the pitot tube during a flight. The pitot tube has at least the front opening. A dynamic pressure corresponding to an airspeed of the aircraft may be obtained by using a pitot tube 121 having no static hole as in a second embodiment, and a separately-provided device having a static hole (a trailing cone device in the second embodiment). Alternatively, the dynamic pressure may be also obtained by detecting the total pressure and the static pressure by a pitot tube having both the front opening and the static hole.

In the present invention, various devices installed outside the airframe for various purposes, such as a camera that photographs a photographing object (e.g., a ground surface) from outside the airframe, may be provided on the penetration member in addition to the detection device that detects the physical quantity as described above.

The present invention may be also applied to railway vehicles that run at high speed in addition to the aircraft. Examples of the railway vehicles include superconducting magnetic levitation linear motor cars. In the railway vehicles, there exists the same problem as that described above for the aircraft when it is necessary to install a device outside the vehicle for a running test or the like.

A railway vehicle according to the present invention includes: a penetration member that penetrates a structure body between an inside and an outside via an opening provided in the structure body; a seal that seals a gap set between an opening formation member forming the opening and the penetration member; and a retainer that presses the seal against the penetration member and the opening formation member, wherein each of the penetration member and the opening formation member includes a receiving section that receives the seal, both of the receiving sections are arranged along a direction connecting one side and the other side of the gap with the gap therebetween, and the seal is fixed to only one of the receiving section of the penetration member and the receiving section of the opening formation member.

In accordance with the present invention, it is possible to reliably hold airtightness inside the airframe even when the member penetrating the airframe (or the structure body) between the inside and the outside is deformed by the aerodynamic load.

BRIEF DESCRIPTION OF THE DRAWINGS

FIG. 1A is a view illustrating the entire aircraft; and FIG. 1B is a view illustrating a measuring device that is attached to an airframe of the aircraft via a window (an enlarged view of a range indicated by an alternate long and short dash line in FIG. 1A);

FIG. 3A is an entire perspective view of the arm; and FIG. 3B is an exploded perspective view of the arm;

FIG. 8A is a view illustrating a front portion of a fuselage of the aircraft; and FIG. 8B is a view illustrating a pitot device that is attached to an airframe via a window;

DETAILED DESCRIPTION OF THE PREFERRED EMBODIMENTS

In the following, embodiments of the present invention are described by reference to the accompanying drawings.

[First Embodiment]

Figure 1B:
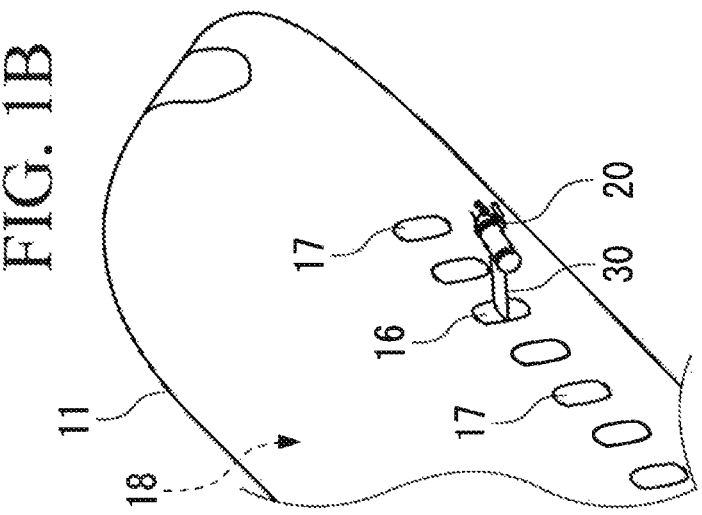
FIGS. 1A and 1B show an aircraft according to a first embodiment.
Figure 1A:
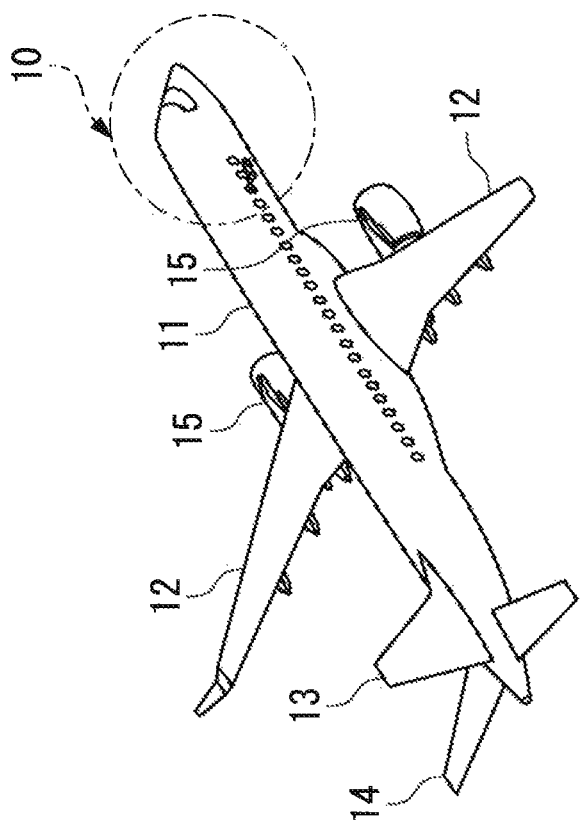

As shown in FIG. 1A, an aircraft 10 includes a fuselage 11, main wings 12 and 12 provided to the right and left of the fuselage 11, a vertical stabilizer 13, and a horizontal stabilizer 14. Engines 15 and 15 are respectively supported on the main wings 12 and 12.

In the present specification, "front" means a nose side of the aircraft 10, and "rear" means a tail side of the aircraft 10.

Also, "upper" means an upper side of an airframe of the aircraft 10, and "lower" means a lower side of the airframe of the aircraft 10.

In a test flight, a measuring device 20 is attached to the airframe of the aircraft 10 as shown in FIG. 1B. The measuring device 20 is installed outside the airframe in order to obtain icing conditions on the airframe. The measuring device 20 is fixed to an arm (a penetration member) 30 that extends out of the airframe from a window 16 provided on a right side wall of the airframe.

To avoid a decrease in aerodynamic performance due to ice accretion on the airframe (particularly, the main wings 12), it is necessary to check performance of a device for melting ice or the like by monitoring the icing conditions.

The window 16 is located on a front side in a cabin 18.

To install the measuring device 20, the window 16 is composed of a window upper portion 8A and a window lower portion 8B (FIG. 5), which constitute a window substitute member (an opening formation member), instead of an existing resin panel formed of an acrylic resin or the like. The resin panels are installed on other windows 17 provided in the cabin 18.

A more specific configuration of the window 16 is described later.

The measuring device 20 measures a diameter of water droplets included in the atmosphere, and a mass of water per unit volume in the atmosphere. A measuring unit that measures the diameter of water droplets in the atmosphere by using a laser beam is provided at a front end of the measuring device 20. Measuring units that respectively measure the mass of water per unit volume in the atmosphere and a pressure of the atmosphere are also provided at the front end of the measuring device 20.

A measurement value by the measuring device 20 is transmitted to a control device inside the airframe through an electric line (not shown) provided in the measuring device 20. A device that measures an amount of ice accretion, and a device that measures an atmospheric pressure are provided at a plurality of positions of the airframe.

The control device continuously monitors the icing conditions including whether or not ice accretes and ice growth conditions by appropriately using the diameter of water droplets and the mass of water droplets per unit volume transmitted from the measuring device 20, the amount of ice accretion and the atmospheric pressure transmitted from the other measuring devices, or the like. The control device checks the performance of the device for melting ice accreting to the airframe by heat based on the icing conditions.

To accurately obtain the icing conditions, it is desirable to install the measuring device 20 at a position where a unidirectional uniform flow or an airflow in a state close thereto is formed. Therefore, the measuring device 20 is preferably installed apart a predetermined distance from an airframe surface where a boundary layer is formed, and within a range in which the fuselage 11 extends with a constant diameter. The measuring device 20 is also preferably installed on a side ahead of the main wings 12 where a stable airflow is formed by avoiding a rear side of the main wings 12. The front side in the cabin 18 falls under a position close to the uniform flow.

An appropriate installment position for the measuring device 20 is selected so as not to affect entire aerodynamic characteristics of the aircraft 10 by attaching the measuring device 20 to the airframe, and further not to cause aerodynamic interference between the measuring device 20 and another device.

Figure 2:
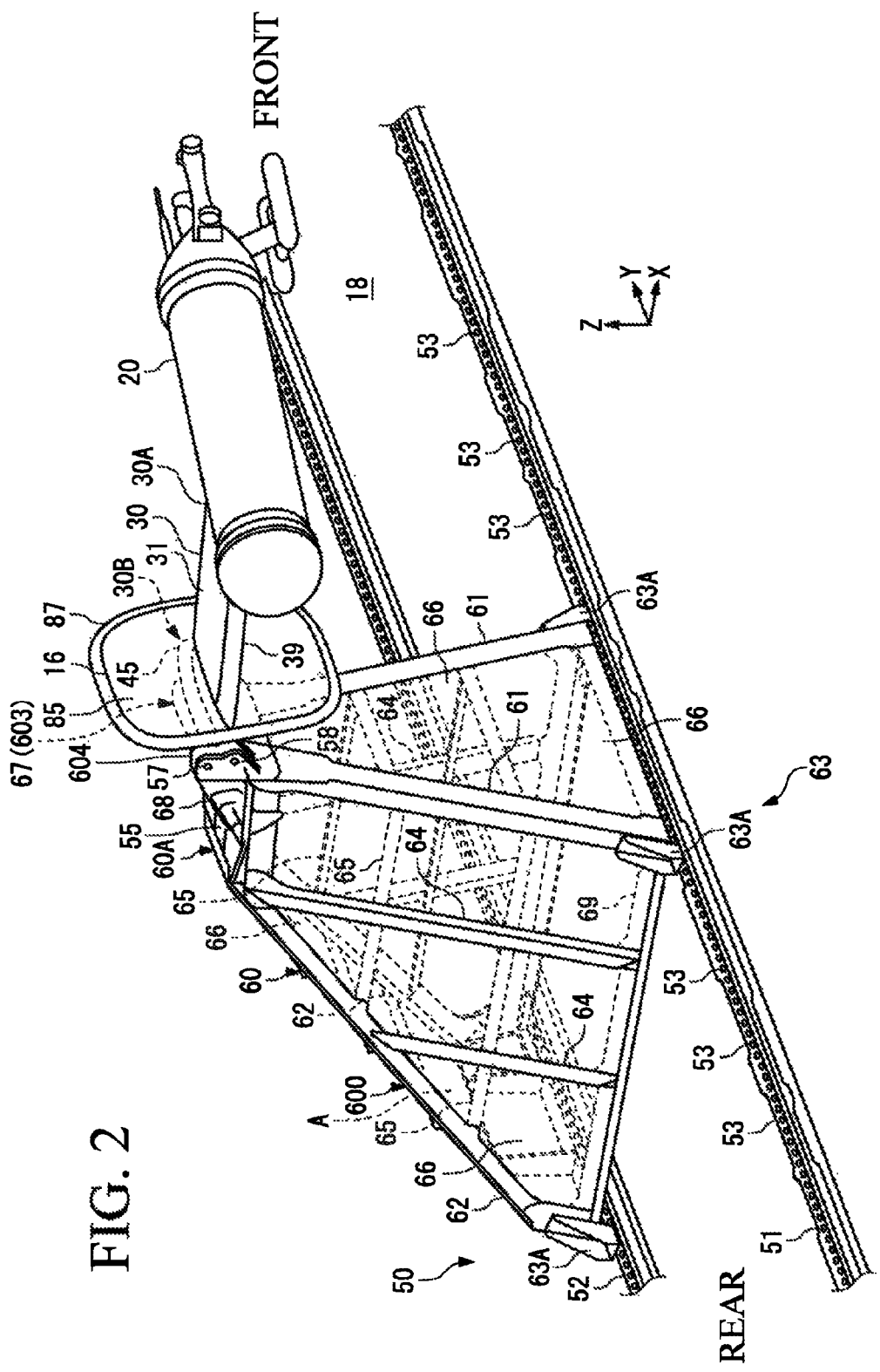
FIG. 2 is a view illustrating a structure for supporting the measuring device and an arm on the airframe.

The arm 30 penetrates the airframe between the inside and the outside via the window 16. As shown in FIG. 2, the arm 30 has a distal end (a first portion 30A) to which the measuring device 20 is fixed, and a proximal end (a second portion 30A) 30B that is coupled to a support device 50 provided inside the airframe. The arm 30 projects to an airframe outer side substantially perpendicular to the fuselage 11.

The arm 30 has a box structure similarly to the main wings 12 in order to obtain a light-weight and highly-rigid structure. The arm 30 is also formed in a thin wing shape in cross section in order to decrease air resistance and prevent generation of a turbulent airflow (a buffet) by the arm 30.

As shown in FIGS. 3A and 3B, the arm 30 includes skins 31 and 32 that are arranged on upper and lower sides, a front spar 33 and a rear spar 34 that connect the skins 31 and 32 respectively on front and rear sides, a plurality of ribs 35 to 37 that support the skins 31 and 32 from inside, and a front edge 38 and a rear edge 39 that are located at a front and a rear of the arm 30. The constituent components of the arm 30 can be formed of a metal material such as aluminum alloy. The constituent components may be also formed of a fiber reinforced resin containing reinforcement fiber such as carbon fiber.

The end rib 37 (FIG. 3B) located at the distal end 30A of the arm 30 has a flange 371 to which the measuring device 20 is fixed. The measuring device 20 is detachably fixed to the flange 371 by fasteners.

The electric line provided in the measuring device 20 is led into the arm 30 from an opening 370 formed in the end rib 37, and is wired along the lower skin 32. Openings 350 and 360 for passing the electric line are respectively formed in the ribs 35 and 36.

The lower skin 32 is divided into two panels 32A and 32B on the proximal end 30B side. The electric line can be laid by removing the larger panel 32B.

A coupling section 43 that is coupled to the support device 50 on an inner side of the window 16 is provided at an end portion on an airframe inner side of the front spar 33.

A coupling section 44 that is coupled to the support device 50 on the inner side of the window 16 is also provided at an end portion on the airframe inner side of the rear spar 34.

The pair of coupling sections 43 and 44 project to the airframe inner side with respect to airframe inner end portions 311 and 321 (FIG. 3B) of the skins 31 and 32 (FIG. 3A).

Two holes 431 and 432 are formed penetrating the coupling section 43 in a front-rear direction. The holes 431 and 432 are arranged in an up-down direction.

Two holes 441 and 442 similar to the above holes 431 and 432 are also formed in the coupling section 44.

The coupling sections 43 and 44 are coupled to a pair of coupling sections provided in the support device 50 by pins 57 and 58 (FIG. 2) that are respectively inserted through the two holes formed in each of the coupling sections 43 and 44. The arm 30 is fixed to the support device 50 by coupling together the coupling sections of the arm 30 and the support device 50 by the two pins 57 and 58.

It is necessary to maintain pressurization inside the airframe by ensuring airtightness between the arm 30 and the window 16 on the proximal end 30B-side of the arm 30. A seal fixing section (a receiving section) 45 (FIG. 3A) to which an airtightness holding section 70 described later is fixed is provided on an outer periphery on the proximal end 30B-side of the arm 30.

The seal fixing section 45 is composed of a pair of components 45U and 45D that are arranged on the upper and lower sides as shown in FIG. 3B.

The seal fixing section 45 is formed in a rectangular shape as a whole, and is arranged perpendicular to an axial direction D0 of the arm 30. The axial direction D0 of the arm 30 corresponds to a penetration direction in which the arm 30 penetrates the airframe. The front spar 33 and the rear spar 34 penetrate the seal fixing section 45 via a space surrounded by the components 45U and 45D. The coupling section 43 of the front spar 33 and the coupling section 44 of the rear spar 34 are located on the airframe inner side with respect to the seal fixing section 45.

An electric line leading section 46 through which the electric line is led out from inside the arm 30 is provided between the coupling sections 43 and 44. A gap between the coupling sections 43 and 44 is closed by another fitting 461 (FIG. 3B) attached to the electric line leading section 46.

The electric line is led out into the airframe through an opening 460 formed in the electric line leading section 46, and is connected to the control device. A gap between a peripheral edge portion of the opening 460 and the electric line is sealed by the fitting 461 and a seal (not shown).

The front edge 38 and the rear edge 39 are formed shorter than a length of the skins 31 and 32. Airframe inner end portions 381 and 391 (FIG. 3B) of the front edge 38 and the rear edge 39 are offset toward the airframe outer side with respect to the airframe inner end portions 311 and 321 of the skins 31 and 32 (see FIG. 3A). Accordingly, an accommodation space 47 (FIG. 3A) that accommodates a portion of the window 16 is formed between the airframe inner end portion 381 of the front edge 38 and the seal fixing section 45, and between the airframe inner end portion 391 of the rear edge 39 and the seal fixing section 45.

The arm 30 is grounded to a frame of the fuselage 11 by a bonding jumper (not shown) for a lightning strike on the arm 30 and the measuring device 20.

The arm 30 projects to the airframe outer side from the window 16 as shown in FIG. 2. The arm 30 and the measuring device 20 generate air resistance during a flight.

Moreover, lift is applied to the arm 30 during a flight. Since the arm 30 is formed in a wing shape in section, large lift is applied.

It is necessary for the support device 50 to have rigidity enough to receive a large aerodynamic load applied to the arm 30 and the measuring device 20 due to the air resistance and the lift, and to reliably support the arm 30 without being deformed even when the aerodynamic load is input.

The support device 50 includes two seat rails 51 and 52 (also called seat tracks) that support seats (not shown) within the cabin 18, and a mount 60 that is provided on the seat rails 51 and 52 as shown in FIG. 2.

The seat rails 51 and 52 extend parallel to each other in the front-rear direction within the cabin 18, and are installed on a floor of the cabin 18.

The seats are fixed to the seat rails 51 and 52 by fixtures (not shown). A plurality of engagement sections 53 (holes) with which the fixtures can be engaged are formed at a predetermined interval in a length direction in each of the seat rails 51 and 52. A seat position can be adjusted by selecting the appropriate engagement sections 53.

The seat rails 51 and 52 support the seats and passengers sitting in the seats. A large load is applied thereto in an emergency accompanied by a steep turn or a speed change of the airframe. Since the seat rails 51 and 52 have rigidity necessary for receiving the large load in an emergency, the seat rails 51 and 52 can sufficiently receive the aerodynamic load applied to the arm 30 and the measuring device 20. Thus, the aerodynamic load on the measuring device 20 and the arm 30 is allocated to the seat rails 51 and 52.

The mount 60 is interposed between the seat rails 51 and 52 installed on the floor of the cabin 18, and the arm 30 penetrating the window 16 installed in a wall of the cabin 18.

The mount 60 transmits the aerodynamic load input from the arm 30 to the seat rails 51 and 52. The seat rails 51 and 52 having sufficient rigidity receive the entire aerodynamic load.

In the mount 60, four thin side plates 66 are provided in a framework 600 having a vaulting horse shape that is installed on the seat rails 51 and 52 as shown in FIG. 2.

Two first braces 61 and 61 constituting the framework 600 rise from the seat rail 51 located immediately below the window 16 toward a front surface of the window 16. Two second braces 62 and 62 similarly constituting the framework 600 obliquely rise from the seat rail 52 toward the front surface of the window 16. The aerodynamic load input from the arm 30 is transmitted to the seat rails 51 and 52 mainly through the first braces 61 and 61, the second braces 62 and 62, and a top plate 55 located at an upper end portion 60A.

The framework 600 includes a plurality of longitudinal reinforcements 64, a plurality of lateral reinforcements 65, a tension member 63 that fixes the braces 61, 61, 62, and 62 to the seat rails 51 and 52, and a pair of coupling members 67 and 68 that are coupled to the coupling sections 43 and 44 at the proximal end 30B of the arm 30 in addition to the first braces 61 and 61, and the second braces 62 and 62.

The four side plates 66 form four side walls of the mount 60, and connect together the braces 61, 61, 62, and 62 adjacent to each other. The top plate 55 forms an upper wall of the mount 60, and connects the braces 61, 61, 62, and 62. The side plates 66 and the top plate 55 receive an in-plane shear force of the walls of the mount 60, and reinforce the framework 600. The mount 60 keeps its shape without being deformed by the load input from the arm 30.

The mount 60 is fixed to the appropriate engagement sections 53 on the seat rails 51 and 52 by the tension member 63 that is fixed to a frame body 69 fixed to lower ends of the first braces 61 and 61 and the second braces 62 and 62.

The tension member 63 is composed of components 63A respectively fixed to the lower ends of the first braces 61 and 61 and the second braces 62 and 62. The tension member 63 is detachably fixed to the appropriate engagement sections 53 on the seat rails 51 and 52.

The tension member 63 resists a tensile load and a compressive load transmitted through the braces 61, 61, 62, and 62 from the arm 30 while distributing the loads to the respective components 63A, so that the braces 61, 61, 62, and 62 are reliably fixed to the seat rails 51 and 52. Accordingly, it is secured that the aerodynamic load is sufficiently transmitted to the seat rails 51 and 52 through the braces 61, 61, 62, and 62.

Coupling receiving sections 603 and 604 are provided at the upper end portion 60A of the mount 60 where upper ends of the first braces 61 and 61 and the second braces 62 and 62 are gathered.

The coupling member 68 has the coupling receiving section 604 that projects toward the window 16 from the top plate 55. Two holes are arranged in the up-down direction in the coupling receiving section 604. The coupling receiving section 604 and the coupling section 44 (FIG. 3A) are coupled together by the pins 57 and 58 (FIG. 2) that are respectively inserted through the two holes. The pins 57 and 58 are both arranged along the front-rear direction, and provided detachably from the coupling receiving section 604 and the coupling section 44.

The coupling member 67 has the coupling receiving section 603 similar to the coupling receiving section 604. Two holes are arranged in the up-down direction in the coupling receiving section 603. The coupling receiving section 603 and the coupling section 43 (FIG. 3A) are coupled together by the pins 57 and 58 (FIG. 2) that are respectively inserted through the two holes.

The aerodynamic load applied to the arm 30 and the measuring device 20 is input to the mount 60 through the coupling sections 43 and 44 and the coupling receiving sections 603 and 604.

In the present embodiment, the arm 30 is passed through the airframe via the window 16 in order to attach the measuring device 20 to the airframe of the aircraft 10, and the aerodynamic load applied to the arm 30 and the measuring device 20 is allocated to the seat rails 51 and 52. Therefore, it is not necessary to make large-scale modification, for example, in which an opening for passing the arm 30 is provided by breaking a portion of the airframe, and a structural member of the airframe is reinforced around the opening so as to receive the aerodynamic load. It is thus possible to easily attach the measuring device 20 to the airframe by replacing the resin panel of the window 16 with the window substitute member (the window upper portion 8A and the window lower portion 8B), and installing the mount 60 and the arm 30 without modifying the airframe.

The mount 60, the seat rails 51 and 52, the arm 30, and the window substitute member are detachably coupled together by fasteners. Moreover, the window substitute member can be replaced with the original resin panel by using clips in a similar manner to that in the window panel replacement. Thus, the airframe can be easily restored to the original state.

Since the airframe is not modified at the time of attaching the measuring device 20 as described above, it is not necessary to perform a restoration work accompanying the modification.

As a result, it is possible to significantly reduce labor, cost, and work time by eliminating the large-scale modification required for installing the measuring device 20 and the restoration work accompanying the modification.

Next, a configuration of the window 16 is described, and the airtightness holding section 70 that holds airtightness at a position where the arm 30 penetrates the window 16 is subsequently described.

Figure 4:
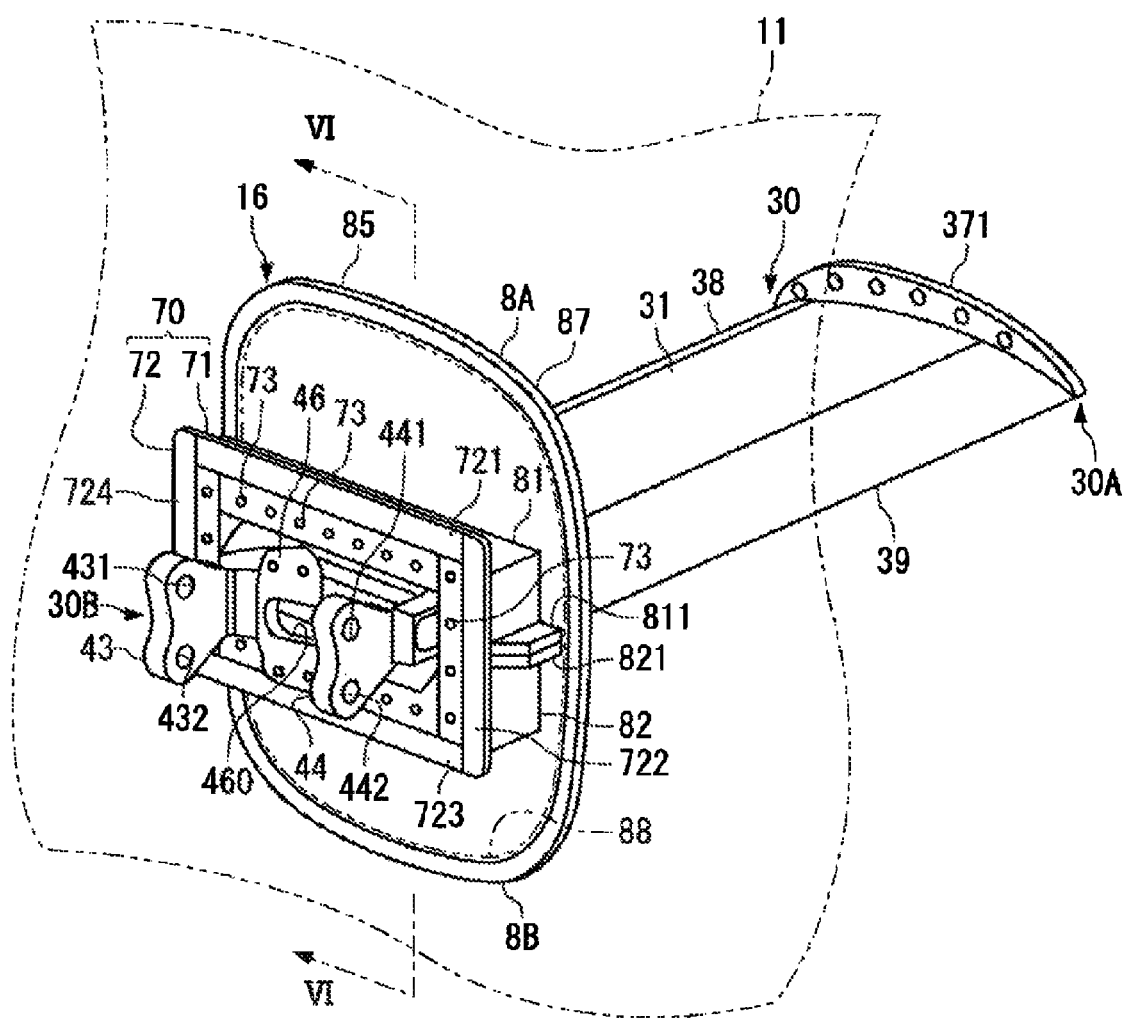
FIG. 4 is a view illustrating the arm, a window, and a sealing section.
Figure 5:
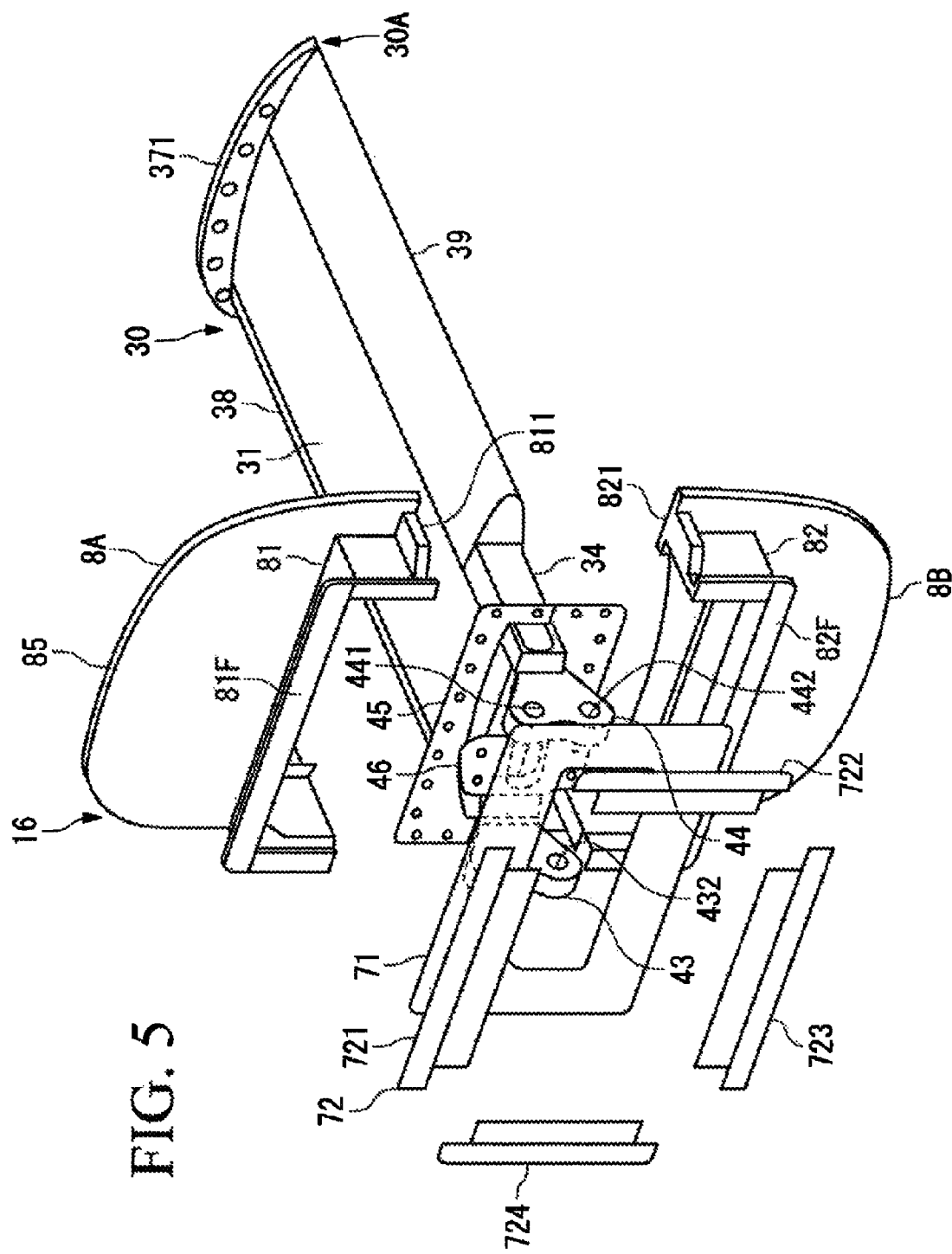
FIG. 5 is an exploded view of the window and the sealing section.
Figure 6:
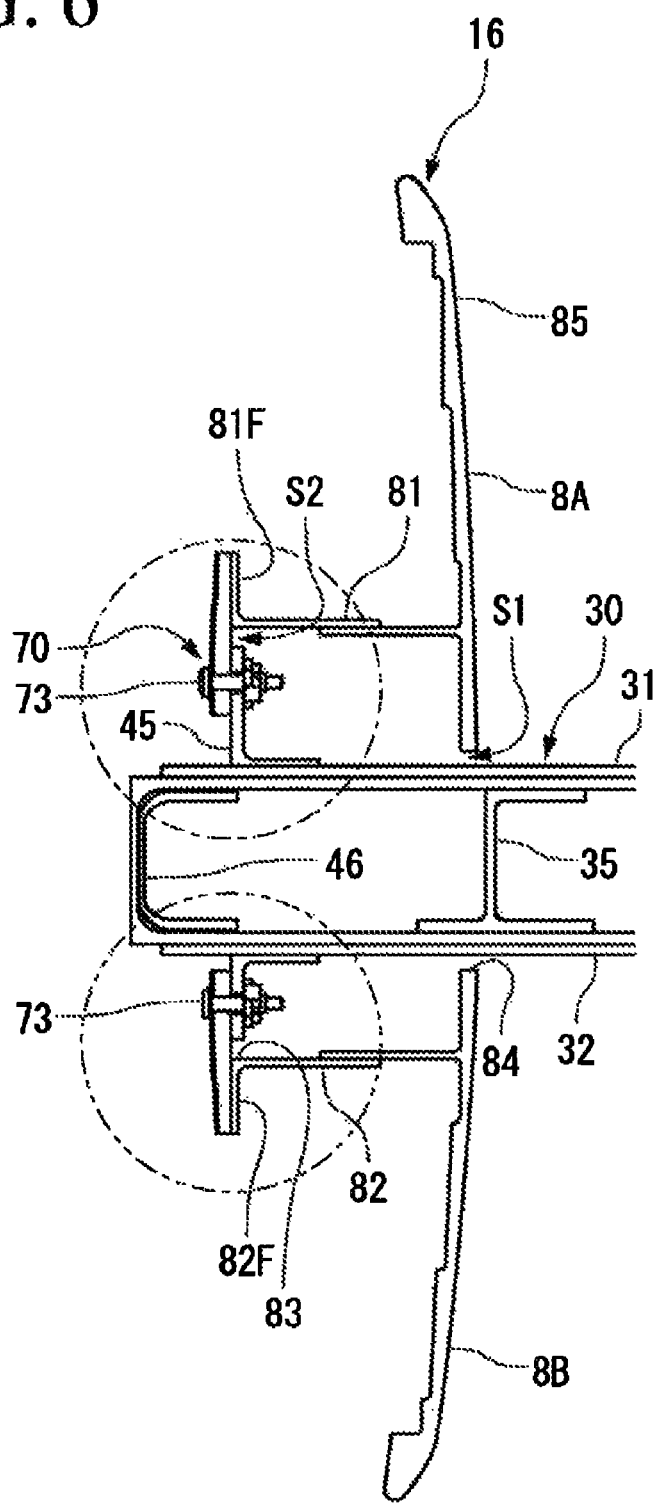
FIG. 6 is a view along an arrow VI-VI in FIG. 4.

As shown in FIGS. 4, 5, and 6, the window 16 includes a metal panel 85, a reinforcement (not shown) that is provided on a surface on the airframe inner side of the metal panel 85, and an upper support 81 and a lower support 82 that rise from the surface on the airframe inner side of the metal panel 85.

Figure 11:
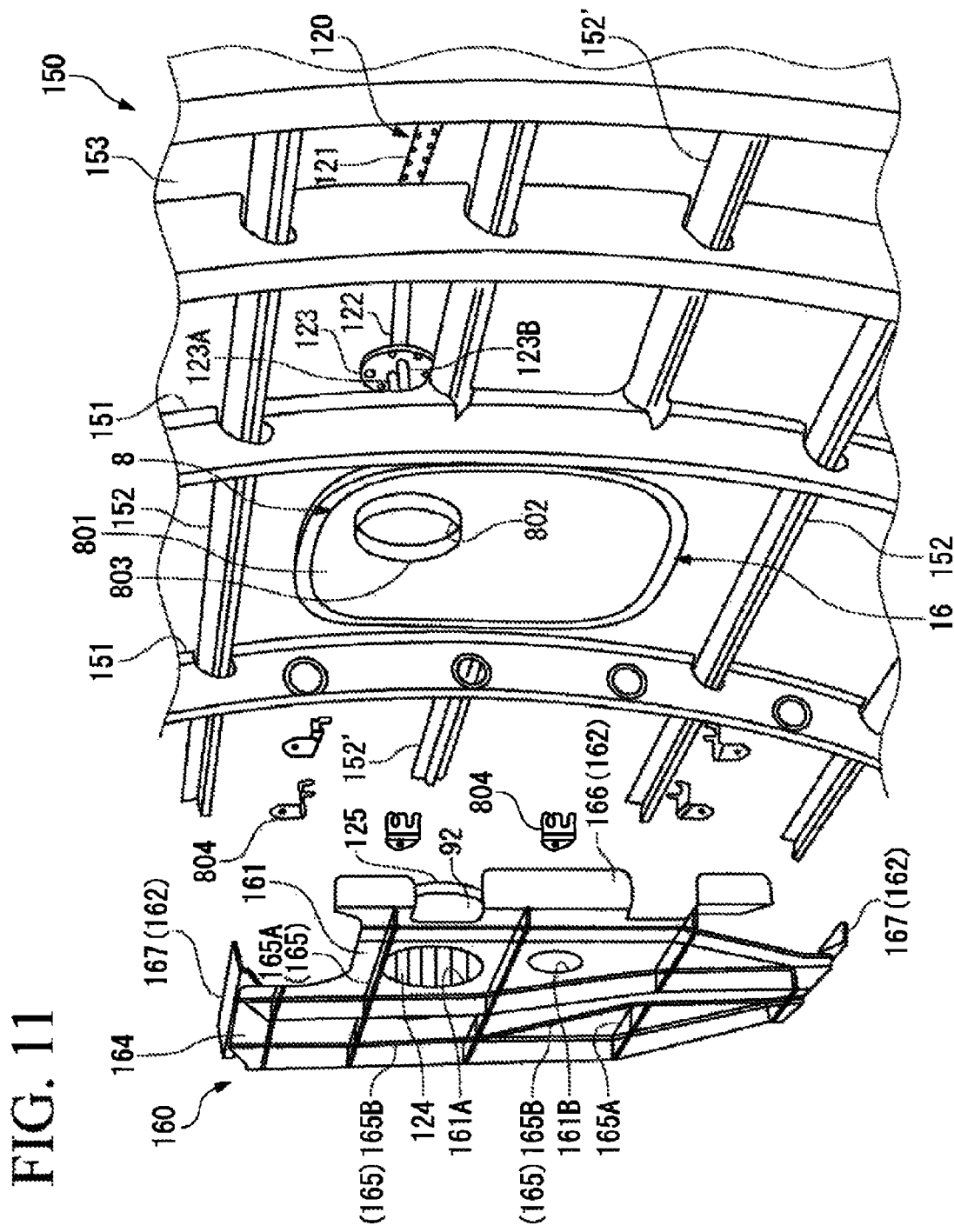
FIG. 11 is a view illustrating structural members of the airframe, the window substitute member, and a load transmission member that transmits an aerodynamic load to the structural members.

The metal panel 85 is fixed to a window frame 88 (FIG. 4) that is formed on a skin of the fuselage 11 from the airframe inner side by using a plurality of clips (not shown) (see a clip 804 in FIG. 11). A gap between an outer periphery of the metal panel 85 and an inner periphery of the window frame 88 is sealed by a gasket 87 (FIG. 2) made of rubber. The clips and the gasket 87 are similar to those provided in the window 17.

The window 16 of the present embodiment is divided into upper and lower halves, and includes the window upper portion 8A and the window lower portion 8B as shown in FIG. 5. The arm 30 and the window 16 can be assembled together by sandwiching the arm 30 from the upper and lower sides between the window upper portion 8A and the window lower portion 8B.

The upper support 81 is provided on the airframe inner side of the window upper portion 8A. The lower support 82 is provided on the airframe inner side of the window lower portion 8B. The upper support 81 and the lower support 82 form a box-shaped structure that surrounds the outer periphery of the arm 30. The upper support 81 and the lower support 82 are accommodated in the accommodation spaces 47 of the arm 30.

The upper support 81 and the lower support 82 are fixed by a fixing section 811 and a fixing section 821 that are formed on right and left sides in front view of the window 16.

Accordingly, a panel opening 84 is formed in the metal panel 85, and a support opening (an opening) 83 is formed on an inner side of the upper support 81 and the lower support 82 as shown in FIG. 6. The arm 30 penetrates the window 16 via the panel opening 84 and the support opening 83.

The panel opening 84 is slightly larger than an outer shape of the arm 30 at the accommodation spaces 47 (FIG. 3A). A gap S1 having a predetermined dimension is set over an entire periphery of the panel opening 84 between the arm 30 and the metal panel 85.

The support opening 83 is slightly larger than an outer shape of the seal fixing section 45 of the arm 30.

As shown in FIGS. 5 and 6, flanges (receiving sections) 81F and 82F that extend outward from the support opening 83 are respectively formed on the airframe inner side of the upper support 81 and the lower support 82. A gap S2 (FIG. 6) having a predetermined dimension is set over an entire periphery of the support opening 83 between inner peripheries of the flanges 81F and 82F and an outer periphery of the seal fixing section 45. The flanges 81F and 82F are arranged flush with a surface on the airframe inner side of the seal fixing section 45 with the gap S2 therebetween.

The flanges 81F and 82F function as a seal receiving section that receives a seal 71 together with the seal fixing section 45. By providing the upper support 81 and the lower support 82 in a box shape as described above, the seal receiving section that receives the seal 71 can be easily provided on the member of the window 16 as the flanges 81F and 82F of the upper support 81 and the lower support 82 along a direction perpendicular to the axial direction of the arm 30. By sliding the seal 71 along the flanges 81F and 82F as described later, it is possible to prevent load input from the arm 30 to the window 16.

Figure 7A:
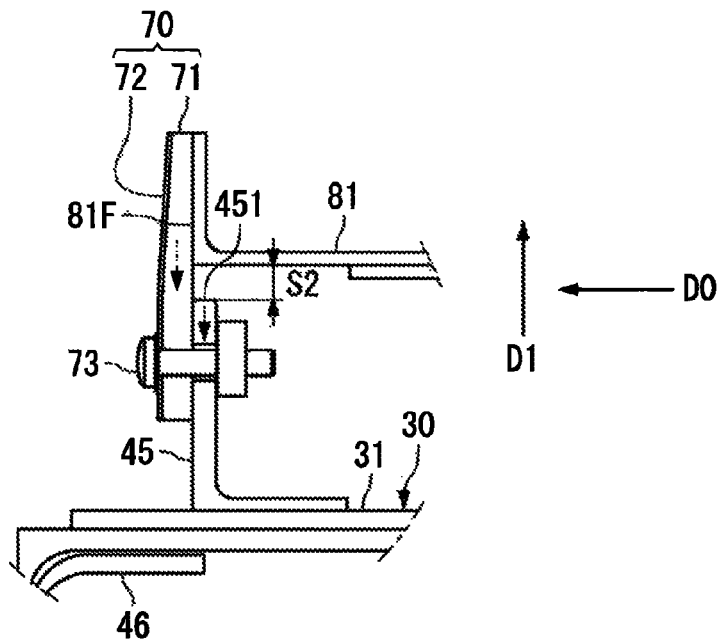
FIG. 7A shows an upper portion of an airtightness holding section (an enlarged view of a range indicated by an alternate long and short dash line in FIG. 6)

Both of the flanges 81F and 82F as the seal receiving section and the seal fixing section 45 in the present embodiment are arranged along a direction D1 connecting one side and the other side of the gap S2 with the gap S2 therebetween as shown in FIG. 7A. The gap S2 is formed with the seal fixing section 45 and the flanges 81F and 82F facing each other. A direction connecting the seal fixing section 45, which is one of the members forming the gap S2, and the flanges 81F and 82F, which are the other of the members forming the gap S2, corresponds to the direction D1 connecting one side and the other side of the gap S2. In the present embodiment, the direction D1 connecting one side and the other side of the gap S2 corresponds to a direction perpendicular to or substantially perpendicular to the axial direction D0 of the arm 30. Therefore, the seal fixing section 45 and the flanges 81F and 82F are arranged along the direction perpendicular to or substantially perpendicular to the axial direction D0 of the arm 30.

Next, the airtightness holding section 70 is described.

As shown in FIGS. 4 and 6, the airtightness holding section 70 includes the seal 71 that seals the gap S2, and a retainer 72 that presses the seal 71. The seal 71 and the retainer 72 extend along the seal fixing section 45 and the flanges 81F and 82F arranged with the gap S2 therebetween.

The seal 71 is formed in a frame shape. The seal 71 seals the gap S2 between the flanges 81F and 82F of the window 16 and the seal fixing section 45 of the arm 30.

An appropriate rubber material can be used for the seal 71. The seal 71 of the present embodiment is formed of chloroprene rubber having flame retardancy.

The retainer 72 is composed of a plurality of components 721 to 724. The components 721 to 724 are respectively leaf springs, and assembled in a frame shape. The retainer 72 is formed in the same dimension as the seal 71. The retainer 72 presses an entire periphery of the seal 71 toward the flanges 81F and 82F and the seal fixing section 45 from the airframe inner side. For example, the retainer 72 can be formed of a metal material such as aluminum alloy and stainless steel. The retainer 72 has a larger elastic modulus than the material used for the seal 71. The elastic modulus described here is a Young's modulus (a modulus of longitudinal elasticity).

The seal 71 and the retainer 72 are fastened to the seal fixing section 45 by fasteners 73 (FIGS. 4, 6) that penetrate the seal 71 and the retainer 72 in a thickness direction. The plurality of fasteners 73 are arranged at a predetermined interval over the entire periphery of the seal fixing section 45. The seal 71 and the retainer 72 are not fixed to the flanges 81F and 82F by a fastener.

When the fasteners 73 are tightened, the seal 71 is compressed between the retainer 72 and the seal fixing section 45, so that the gap S2 is sealed.

Figure 7B:
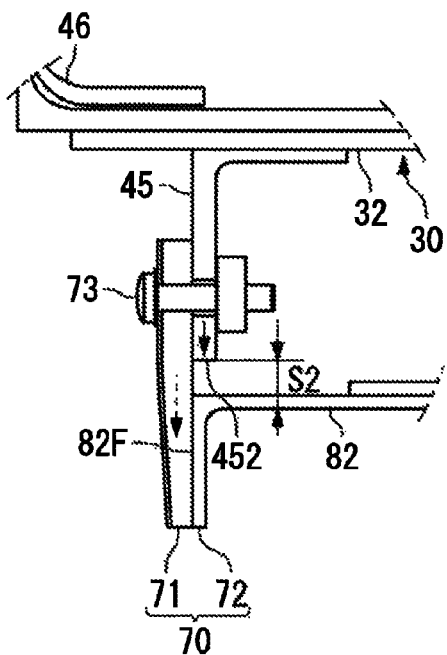
FIG. 7B shows a lower portion of the airtightness holding section (an enlarged view of a range indicated by an alternate long and two short dashes line in FIG. 6)

A portion of the retainer 72 overlapped with the flanges 81F and 82F is slightly inclined toward the airframe outer side with respect to a portion overlapped with the seal fixing section 45 as shown in FIGS. 7A and 7B, so that the retainer 72 reliably presses the seal 71 against the flanges 81F and 82F.

A pressure difference between the pressurization inside the airframe and an atmospheric pressure outside the airframe acts on the seal 71 that seals the gap S2. To hold the pressurization inside the airframe, it is necessary for the seal 71 to closely seal the gap S2.

However, when the atmospheric pressure outside the airframe rapidly drops by an increase in flight altitude particularly right after flight start or the like, the seal 71 is possibly displaced to generate a gap between the seal 71 and the seal fixing section 45 or the flanges 81F and 82F. In order to prevent the problem from happening and hold the pressurization inside the airframe, the seal 71 is pressed against the seal fixing section 45 and the flanges 81F and 82F by the retainer 72.

Here, if the seal 71 and the retainer 72 are fixed to both the seal fixing section 45 and the flanges 81F and 82F, a load is input to the window 16 from the arm 30 when the arm 30 is deformed by the aerodynamic load. The seal 71 may be thereby displaced from the gap S2, or excessively deformed to be separated from the seal fixing section 45 or the flanges 81F and 82F, or the window upper portion 8A and the window lower portion 8B or the window frame 88 may be thereby damaged, so that the airtightness is lost. In order to prevent the problem from happening, the seal 71 is fixed only to the seal fixing section 45. That is, the seal 71 is fixed to the seal fixing section 45 on one end side, and is simply supported by the flanges 81F and 82F on the other end side.

As described above, it is necessary to ensure the airtightness by the seal 71 when the atmospheric pressure outside the airframe drops, and it is also necessary to ensure the airtightness between the arm 30 and the window 16 without transmitting the load from the arm 30 to the window 16 when the arm 30 is deformed by the aerodynamic load. To this end, the gaps S1 and S2 described above are set between the window 16 and the arm 30, the seal 71 that seals the gap S2 is pressed against the window 16 and the arm 30 by the retainer 72, and the seal 71 is fixed on one side.

Since the seal 71 is pressed by the retainer 72, and the seal 71 is fixed to the seal fixing section 45 of the arm 30 on one side as described above, the seal 71 slides against a friction force with the flanges 81F and 82F of the window 16 when the seal fixing section 45 is displaced by the deformation of the arm 30 due to the aerodynamic load.

For example, FIGS. 7A and 7B show an upper end and a lower end of the seal 71, and show a state in which the seal 71 slides downward along the flanges 81F and 82F so as to follow the displacement of the seal fixing section 45 (see a dashed arrow).

By sliding and displacing the seal 71 along the flanges 81F and 82F as described above, the load can be prevented from being directly input to the window 16 from the arm 30.

Note that the seal 71 may be fixed to the flanges 81F and 82F, and may be simply supported by the seal fixing section 45. In this case, by sliding and displacing the seal 71 along the seal fixing section 45, the load can be prevented from being directly input to the window 16 from the arm 30.

Consequently, in the structure in which the seal 71 that holds the airtightness between the arm 30 and the window 16 is pressed by the retainer 72, a mechanism for avoiding load transmission between the arm 30 and the window 16 can be achieved by the configuration in which the seal 71 is fixed to only one of the arm 30 and the window 16, and slidably supported by the other of the arm 30 and the window 16. Because of the mechanism, the airtightness at a position where it is difficult to hold the airtightness due to relative displacement of objects to be sealed (the arm 30 and the window 16) caused by the deformation of the arm 30 due to the aerodynamic load can be reliably held by the seal 71.

In the present embodiment, the measuring device 20 is installed to the right of the airframe. However, the measuring device 20 may be installed at any position such as the left of the airframe, and the upper side and the lower side of the airframe via the arm 30 located outside the airframe.

The measuring device 20 may be also provided on the lower side or the upper side of the arm 30.

If it is not necessary to arrange the measuring device 20 apart from the surface of the airframe, the arm 30 does not need to project long from the window 16, and the measuring device 20 may be provided on the arm 30 close to a surface on the airframe outer side of the window 16.

[Second Embodiment]

Next, a second embodiment of the present invention is described by reference to FIGS. 8 to 13.

Figure 8A:
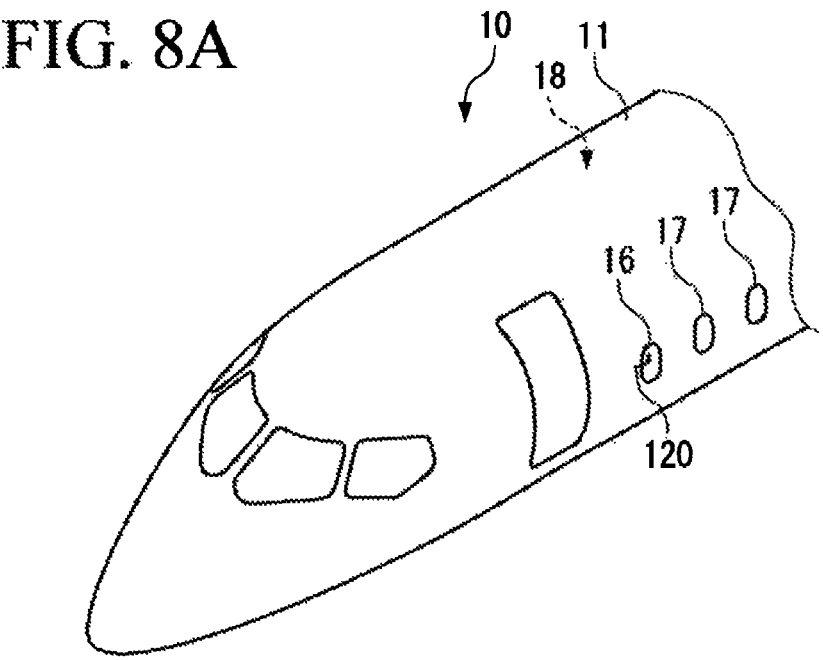
FIGS. 8A and 8B show an aircraft according to a second embodiment.

The aircraft 10 of the present embodiment shown in FIG. 8A is provided with a pitot device (a detection device, a penetration member) 120 in a test flight. The pitot device 120 projects to the airframe outer side from the window 16 of the cabin 18.

The pitot device 120 is provided so as to obtain an accurate airspeed of the aircraft 10 in the test flight together with a trailing cone device (not shown) that trails behind the airframe from an upper end of the vertical stabilizer. The pitot device 120 is removed from the airframe when the task is finished.

The pitot device 120 and the trailing cone device are connected to an arithmetic device of an air data system (not shown).

A pitot device (not shown) that is usually used during a flight of the aircraft 10 is provided on the airframe of the aircraft 10 in addition to the pitot device used in the test flight. The pitot device is permanently provided on the airframe as standard equipment of the aircraft 10.

Figure 8B:
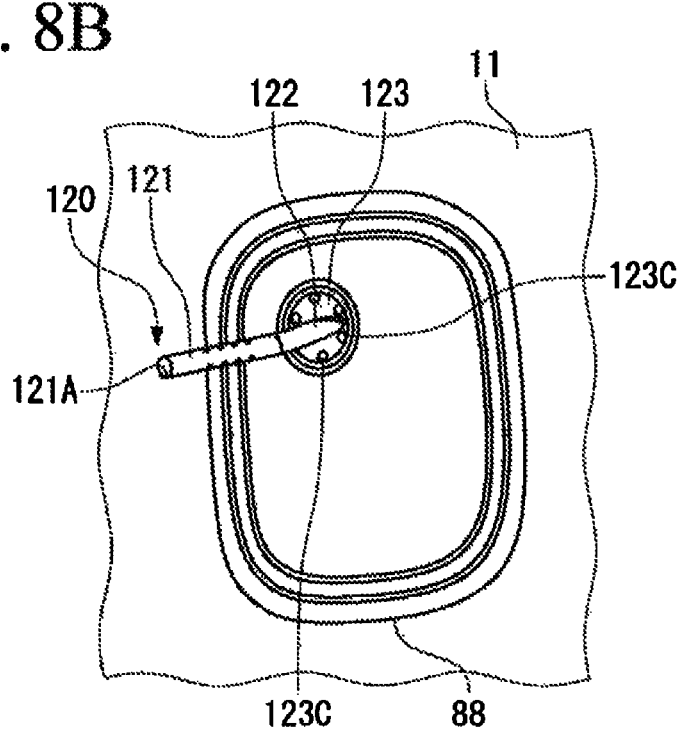

The pitot device 120 includes a pitot tube 121 that opens toward the front side, a pressure detection section 122 that detects a total pressure (also called a full pressure) obtained by the pitot tube 121, and a fixing section 123 that is used for attaching the pitot device 120 to the airframe as shown in FIG. 8B.

The pitot device 120 is grounded to the frame of the fuselage 11 by a bonding jumper (not shown) for a lightning strike.

The pitot device 120 also incorporates a heater that prevents accretion of ice on the pitot tube 121.

The pitot tube 121 has an opening 121A that confronts an airflow. The pitot tube 121 is preferably arranged parallel to the surrounding airflow.

A path leading to the pressure detection section 122 from the opening 121A is formed within the pitot tube 121.

A pressure of air pushed in from the opening 121A during a flight represents the total pressure.

On the other hand, the above trailing cone device measures a static pressure.

The above arithmetic device of the air data system calculates a dynamic pressure and an airspeed based on the total pressure measured by the pitot device 120, and the static pressure measured by the trailing cone device.

That is, a pressure difference between the total pressure and the static pressure represents a dynamic pressure $P_d$ based on the Bernoulli's equation (1).

[Expression 1]

$$v = \sqrt{\frac{2P_d}{\rho}} \quad (1)$$

where v is a flow speed, $P_d$ is a dynamic pressure, and $\rho$ is a fluid density. The flow speed v obtained from the dynamic pressure $P_d$ and the air density $\rho$ corresponds to the airspeed that is a speed of the aircraft 10 relative to airflow.

In order to obtain an accurate dynamic pressure by the pitot device 120, the pitot tube 121 is preferably arranged apart a predetermined distance from the surface of the airframe where a boundary layer is formed.

The pressure detection section 122 connects a proximal end side of the pitot tube 121 and the fixing section 123. The pressure detection section 122 extends in an off-plate direction of the window 16 and toward the front side from the fixing section 123, and is connected to the proximal end side of the pitot tube 121.

Figure 12:
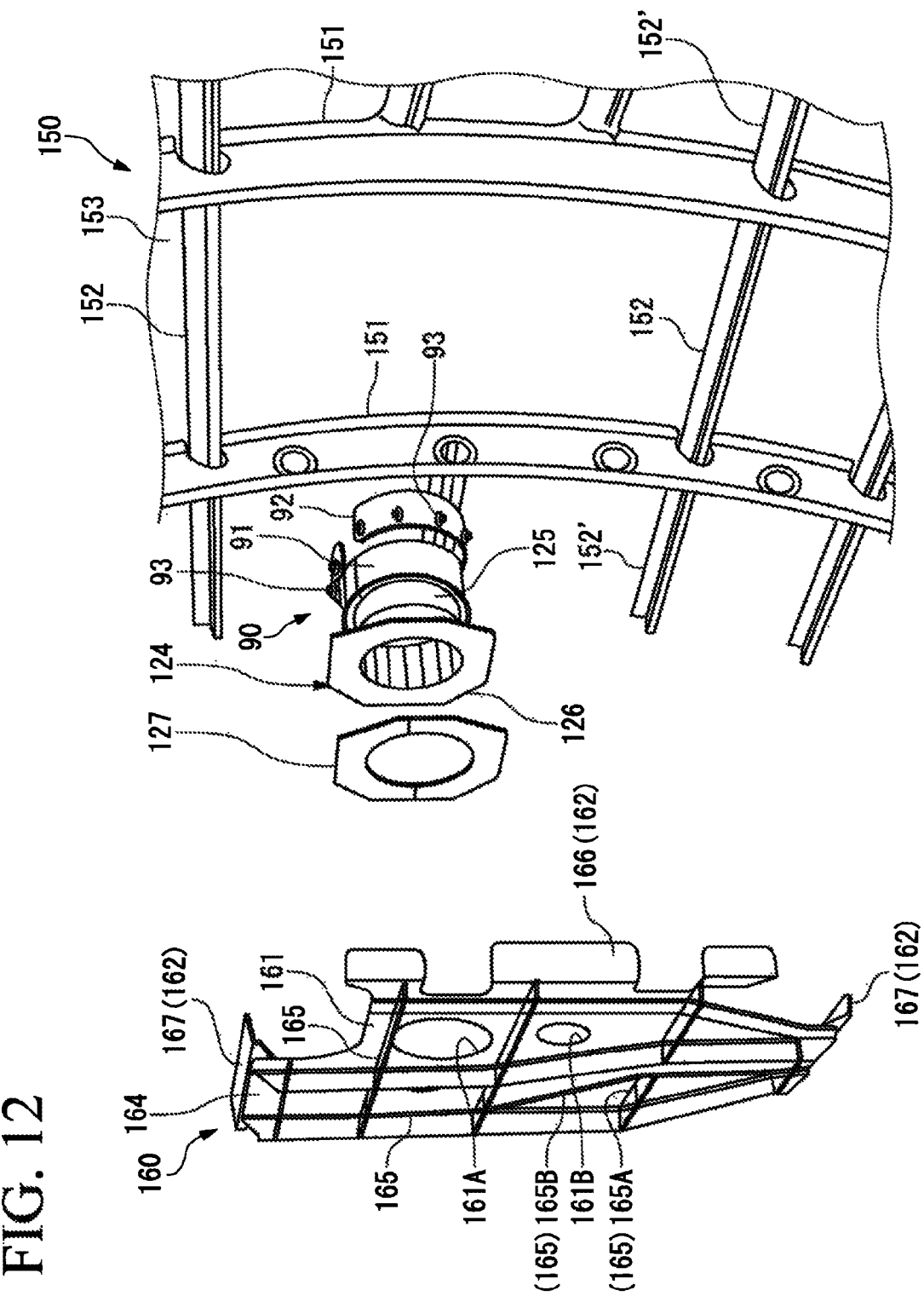
FIG. 12 is an exploded view illustrating a pitot bracket and an airtightness holding section.

The fixing section 123 is integrated with a pitot bracket (a penetration member) 124 that is coupled to a support structure 150 shown in FIGS. 11 and 12. The fixing section 123 and the pitot bracket 124 penetrate the airframe via a circular opening (an opening) 802 in the window substitute member 8 installed in the window 16, to be coupled to the support structure 150 provided inside the airframe.

The fixing section 123 is arranged at an appropriate position on the window substitute member 8 such that the pitot tube 121 is arranged at a position with smallest possible airflow turbulence.

Figure 9:
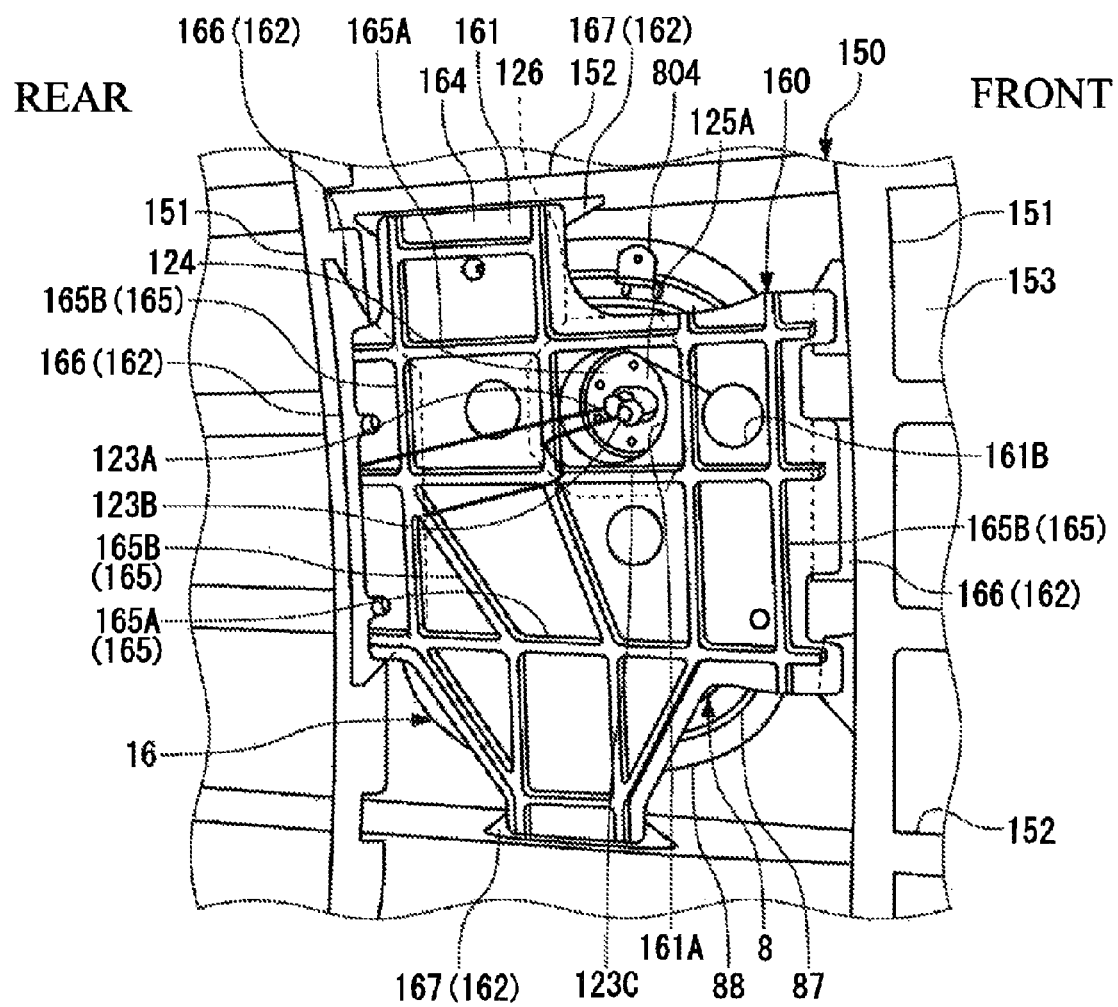
FIG. 9 is a view illustrating the pitot device, a window substitute member, and a support structure (as viewed from an airframe inner side)

As shown in FIG. 9, an electric line leading section 123A that is used for leading out electric lines for an ice protection heater into the airframe, and a total pressure measuring pipe 123B are provided projecting on the airframe inner side of the fixing section 123 that is formed in a disk shape. The led-out electric lines are respectively connected to devices inside the airframe.

The window substitute member 8 is provided in the window frame 88 instead of the resin panel originally provided in the window 16. The window substitute member 8 includes a panel 801 that is formed of a metal material, and a reinforcement (not shown) that is provided on the airframe inner side of the panel 801 as shown in FIG. 11. A peripheral wall 803 that rises toward the airframe inner side is formed on a peripheral edge of the panel opening 802 formed in the panel 801.

The window substitute member 8 is fixed to the window frame 88 from the airframe inner side by using a plurality of clips 804. The clips 804 are fixed to a bracket (not shown) fixed to a skin 153. A gap between the window substitute member 8 and the window frame 88 is sealed by the gasket 87 made of rubber.

Figure 10:
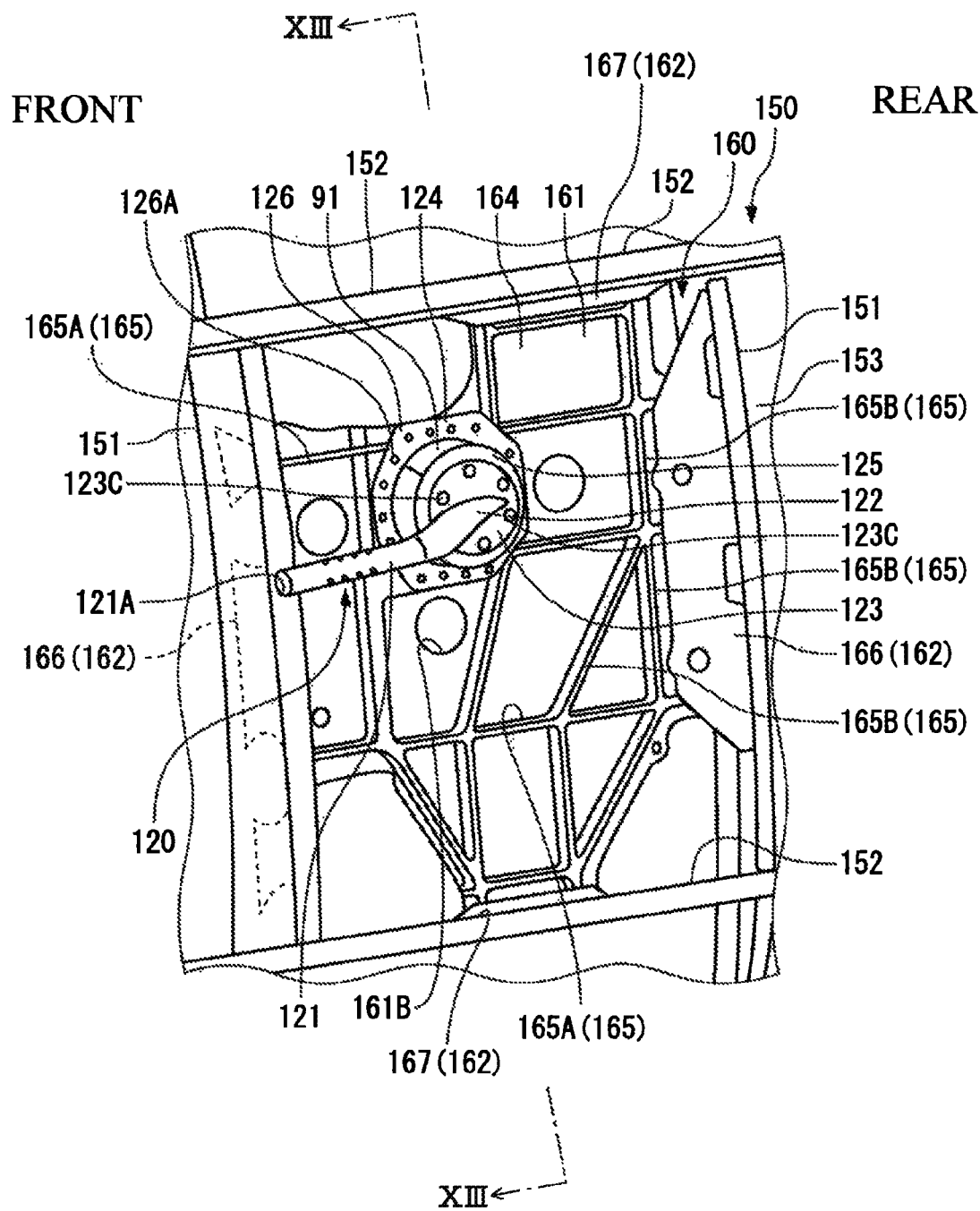
FIG. 10 is a view illustrating the pitot device and the support structure in a state in which the window substitute member is removed (as viewed from an airframe outer side)

As shown in FIGS. 12 and 10, the pitot bracket 124 includes a substantially-cylindrical bracket body 125 that is passed through the panel opening 802 of the window substitute member 8, and a coupling flange 126 that radially extends from an end portion on the airframe inner side of the bracket body 125.

Figure 13:
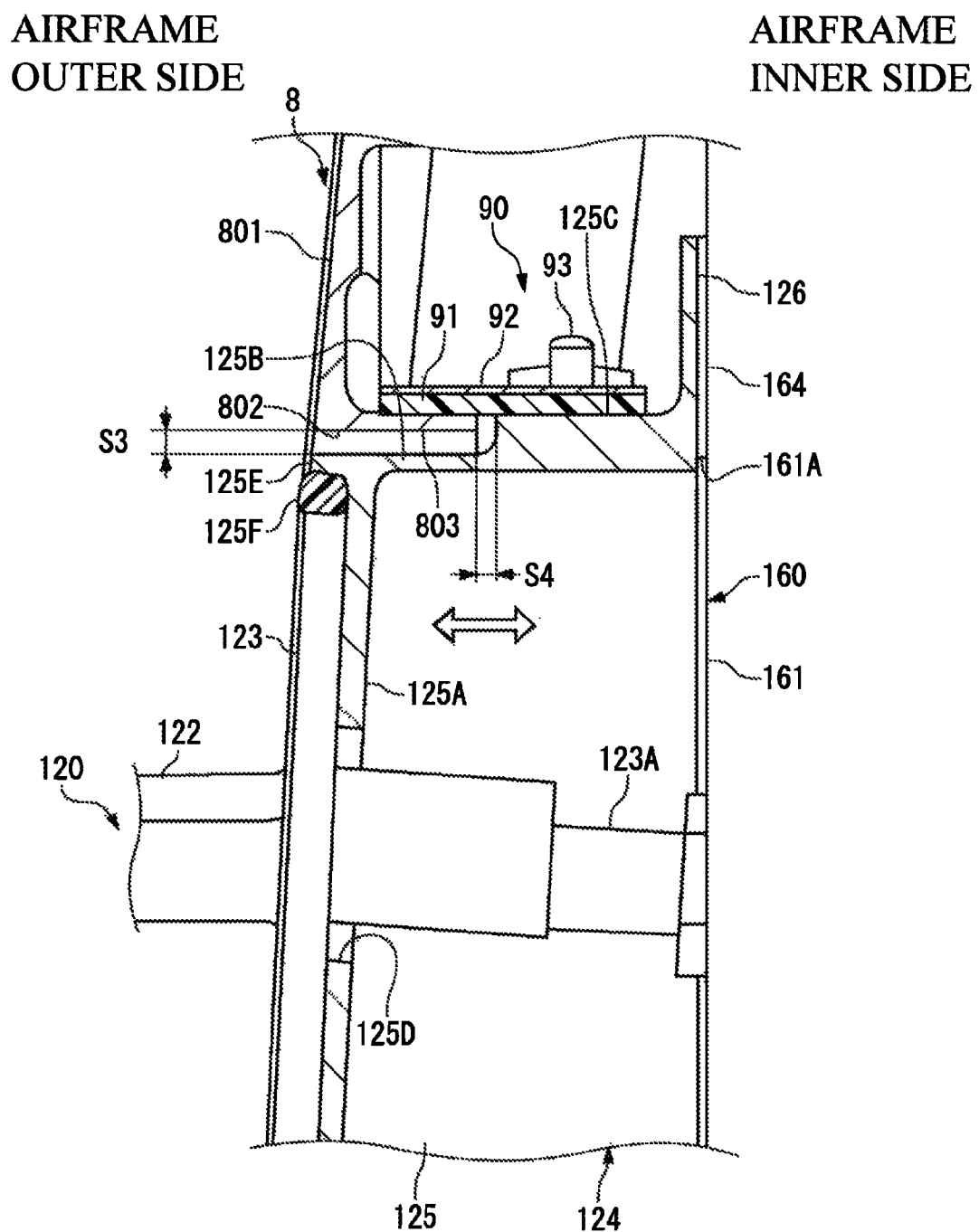
FIG. 13 is a view along an arrow XIII-XIII in FIG. 10.

The fixing section 123 of the pitot device 120 is fastened to a bottom portion 125A (FIG. 9) that is located on the airframe outer side of the bracket body 125 by fasteners 123C as shown in FIG. 10. As shown in FIG. 13, a gap between a peripheral edge of the fixing section 123 and a convex portion 125E that is provided projecting in an annular shape from the bottom portion 125A is sealed by an annular seal 125F.

An insertion hole 125D through which the electric line leading section 123A and the total pressure measuring pipe 123B are passed is formed penetrating the bottom portion 125A in a thickness direction. The insertion hole 125D is partitioned from outside air by the seal 125F, so that airtightness at a position where the electric lines and the pipe are passed is held.

As shown in FIG. 13, an annular side wall of the bracket body 125 is segmented into an airframe outer-side side wall 125B that is arranged on an inner side of the peripheral wall 803 of the panel opening 802 in the window substitute member 8, and an airframe inner-side side wall (an annular portion) 125C whose diameter is increased at a position beyond a distal end of the peripheral wall 803 with respect to an outer diameter of the airframe outer-side side wall 125B (FIG. 13).

A gap S3 having a predetermined dimension is set between an outer peripheral portion of the airframe outer-side side wall 125B and an inner peripheral portion of the peripheral wall 803.

An outer peripheral portion of the airframe inner-side side wall 125C and an outer peripheral portion of the peripheral wall 803 are arranged substantially flush with each other with a gap S4 therebetween. The gap S4 is located between the distal end of the peripheral wall 803 and an end portion of the airframe inner-side side wall 125C.

The outer peripheral portion of the peripheral wall 803 and the outer peripheral portion of the airframe inner-side side wall 125C function as a seal receiving section that receives a seal 91 described later.

Both of the outer peripheral portion of the peripheral wall 803 and the outer peripheral portion of the airframe inner-side side wall 125C as the seal receiving section in the present embodiment are arranged along a direction (see an outlined arrow) connecting one side and the other side of the gap S4 with the gap S4 therebetween as shown in FIG. 13. The gap S4 is formed with the distal end of the peripheral wall 803 and the end portion of the airframe inner-side side wall 125C facing each other. A direction connecting the peripheral wall 803, which is one of the members forming the gap S4, and the airframe inner-side side wall 125C, which is the other of the members forming the gap S4, is the direction connecting one side and the other side of the gap S4, and corresponds to a penetration direction in which the pitot device 120 penetrates the window substitute member 8. Therefore, the outer peripheral portion of the peripheral wall 803 and the outer peripheral portion of the airframe inner-side side wall 125C are arranged along the penetration direction of the pitot device 120.

The coupling flange 126 is fastened to a planar material 164 around a base opening 161A of a load transmission member 160 (described later) by fasteners 126A (FIG. 10). The pitot device 120 and the support structure 150 are thereby coupled together.

A shim 127 (FIG. 12) is interposed between the coupling flange 126 and the planar material 164 if necessary.

The pitot device 120 installed outside the airframe generates air resistance during a flight. The support structure 150 that supports the pitot device 120 has rigidity enough to receive an aerodynamic load applied to the pitot device 120 due to the air resistance or the like.

As shown in FIGS. 9 and 11, the support structure 150 includes frames 151 and stringers 152 that are structural members of the fuselage 11, and the load transmission member 160 that transmits to the frames 151 and the stringers 152 the aerodynamic load input from the pitot device 120 through the pitot bracket 124.

The frames 151 and 151 constituting the support structure 150 are arranged on the front and rear sides with the window 16 therebetween. The stringers 152 and 152 similarly constituting the support structure 150 and perpendicular to the frames 151 and 151 are arranged on the upper and lower sides with the window 16 therebetween. A stringer 152' arranged between the stringers 152 and 152 is interrupted at a position of the window 16.

The frames 151 and 151, and the stringers 152 and 152 are arranged so as to surround the window 16 from all directions.

The load transmission member 160 includes a base 161 that is arranged on the front surface of the window 16, and a plurality of fixing members 162 that fix the base 161 to the frames 151 or the stringers 152.

The base 161 has the planar material 164 that is arranged along the window 16, and a plurality of supports 165 that are provided respectively on a surface on the airframe inner side and a surface on the airframe outer side of the planar material 164.

The aerodynamic load input from the pitot device 120 to the load transmission member 160 through the pitot bracket 124 is transmitted to the frames 151 and the stringers 152 through the load transmission member 160, and is received by the frames 151 and the stringers 152.

The circular base opening 161A is formed in the planar material 164.

The plurality of supports 165 are respectively formed in an inverted T shape in section. The plurality of supports 165 include lateral supports 165A extending in a lateral direction (the front-rear direction) and longitudinal supports 165B extending substantially in a longitudinal direction (the up-down direction).

The aerodynamic load input to the base 161 through the pitot bracket 124 flows toward a peripheral edge of the base 161 through the planar material 164 and the supports 165, and is transmitted to the frames 151 and the stringers 152 through the fixing members 162.

A load toward the rear side and the airframe inner side is applied to the pitot device 120 by the air resistance of the pitot tube 121 and the pressure detection section 122. A load is also applied in the up-down direction by lift and drag acting on the pitot tube 121 and the pressure detection section 122 in no small measure.

Directions of the respective supports 165 are determined so as to ensure rigidity enough to endure the aerodynamic load obtained from combination of the loads, and sufficiently transmit the load to positions of the frames 151 or the stringers 152 to which the base 161 can be fixed.

A hole 161B used for performing a work of attaching a retainer 92 described later is formed in the base 161.

The base 161 is also formed in a shape in which a position of the clip 804 (FIG. 9) provided on the window substitute member 8 is cut away so as to enable adjustment of a fastener for fixing the clip 804 when it is necessary to adjust attachment of the window substitute member 8.

The fixing members 162 have longitudinal fixing members 166 and 166 that respectively fix an end edge portion of the planar material 164 to the frames 151 and 151, and lateral fixing members 167 and 167 that respectively fix the end edge portion of the planar material 164 to the stringers 152 and 152.

Each of the longitudinal fixing members 166 is arranged on the airframe outer side of the planar material 164, and is fastened to the planar material 164 and the frame 151 by a fastener (not shown). In order to avoid stress concentration in the frame 151, the longitudinal fixing member 166 has a shape spreading toward the frame 151 from the planar material 164.

The longitudinal fixing member 166 located on the front side is divided into a plurality of portions in order to avoid interference with a pipe (not shown).

Each of the lateral fixing members 167 is arranged on the airframe outer side of the planar material 164 similarly to the longitudinal fixing member 166, and is fastened to the planar material 164 and the stringer 152 by a fastener (not shown).

In the present embodiment, the pitot device 120 and the pitot bracket 124 are passed through the airframe via the window 16 in order to attach the pitot device 120 to the airframe of the aircraft 10. Therefore, it is possible to easily attach the pitot device 120 to the airframe by replacing the resin panel of the window 16 with the window substitute member 8 and coupling together the load transmission member 160 installed on the structural members of the airframe, and the pitot bracket 124 without modifying the airframe similarly to the first embodiment.

Also, the pitot bracket 124, the load transmission member 160, and the frames 151 and the stringers 152 are detachably coupled together by fasteners. Moreover, the window substitute member 8 can be replaced with the original resin panel by using clips in a similar manner to that in the window panel replacement. Thus, the airframe can be easily restored to the original state.

Next, an airtightness holding section 90 that holds airtightness at a position where the pitot device 120 and the pitot bracket 124 penetrate the window substitute member 8 is described.

As shown in FIGS. 12 and 13, the airtightness holding section 90 includes the seal 91 that seals the gap S4 between the distal end of the peripheral wall 803 of the window substitute member 8 and the end portion of the airframe inner-side side wall 125C of the pitot bracket 124, and the retainer 92 that presses the seal 91. The seal 91 and the retainer 92 extend along the outer peripheral portion of the peripheral wall 803 and the outer peripheral portion of the airframe inner-side side wall 125C arranged with the gap S4 therebetween.

The seal 91 is formed in a band plate shape. The seal 91 is wound over an entire periphery of the outer peripheral portion of the peripheral wall 803 of the window substitute member 8 and the outer peripheral portion of the airframe inner-side side wall 125C of the pitot bracket 124.

An appropriate rubber material can be used for the seal 91. The seal 91 of the present embodiment is formed of chloroprene rubber having flame retardancy.

The retainer 92 is a spring obtained by forming a metal plate in a C shape, and radially exerts an elastic force when wound around an outer periphery of the seal 91. The retainer 92 is formed in the same dimension as the seal 91. The retainer 92 presses the entire periphery of the seal 91 toward the outer peripheral portion of the peripheral wall 803 and the outer peripheral portion of the airframe inner-side side wall 125C. For example, the retainer 92 can be formed of a metal material such as aluminum alloy and stainless steel. The retainer 92 has a larger elastic modulus than the material used for the seal 91. The elastic modulus described here is a Young's modulus (a modulus of longitudinal elasticity).

The seal 91 and the retainer 92 are fastened to the airframe inner-side side wall 125C of the pitot bracket 124 by fasteners 93 that penetrate the seal 91 and the retainer 92 in a thickness direction. The plurality of fasteners 93 are arranged at a predetermined interval in a circumferential direction of the pitot bracket 124. The seal 91 and the retainer 92 are not fixed to the peripheral wall 803 of the window substitute member 8 by a fastener.

When the fasteners 93 are tightened, the seal 91 is compressed between the retainer 92 and each of the peripheral wall 803 and the airframe inner-side side wall 125C, so that the gap S4 is sealed.

A pressure difference between the pressurization inside the airframe and an atmospheric pressure outside the airframe acts on the seal 91 that seals the gap S4. To hold the pressurization inside the airframe, it is necessary for the seal 91 to closely seal the gap S4.

However, when the atmospheric pressure outside the airframe rapidly drops by an increase in flight altitude particularly right after flight start or the like, the seal 91 is possibly displaced to generate a gap between the seal 91 and the peripheral wall 803 or the airframe inner-side side wall 125C. In order to prevent the problem from happening and hold the pressurization inside the airframe, the seal 91 is pressed against the peripheral wall 803 and the airframe inner-side side wall 125C by the retainer 92.

Here, if the seal 91 and the retainer 92 are fixed to both the peripheral wall 803 and the airframe inner-side side wall 125C, a load is input to the window 16 when the aerodynamic load is applied to the pitot device 120. The seal 91 may be thereby displaced from the gap S4, or excessively deformed to be separated from the peripheral wall 803 or the airframe inner-side side wall 125C, or the window substitute member 8 or the window frame 88 may be thereby damaged, so that the airtightness is lost. In order to prevent the problem from happening, the seal 91 is fixed only to the airframe inner-side side wall 125C. That is, the seal 91 is fixed to the airframe inner-side side wall 125C on one end side, and is simply supported by the peripheral wall 803 on the other end side.

As described above, it is necessary to ensure the airtightness by the seal 91 when the atmospheric pressure outside the airframe drops, and it is also necessary to ensure the airtightness between the pitot device 120 and the window 16 without transmitting the load from the pitot device 120 to the window 16 when the pitot device 120 is deformed by the aerodynamic load. To this end, the gaps S3 and S4 described above are set between the window 16 and the pitot device 120, the seal 91 that seals the gap S4 is pressed against the window 16 and the pitot device 120 by the retainer 92, and the seal 91 is fixed on one side.

Since the seal 91 is pressed by the retainer 92, and the seal 91 is fixed to the airframe inner-side side wall 125C of the pitot device 120 on one side as described above, the seal 91 slides against a friction force with the peripheral wall 803 of the window 16 when the airframe inner-side side wall 125C is displaced by the pitot device 120 to which the aerodynamic load is applied.

By sliding and displacing the seal 91 along the peripheral wall 803 as described above, the load can be prevented from being directly input to the window 16 from the pitot device 120.

Note that the seal 91 may be fixed to the peripheral wall 803, and may be simply supported by the airframe inner-side side wall 125C. In this case, by sliding and displacing the seal 91 along the airframe inner-side side wall 125C, the load can be prevented from being directly input to the window 16 from the pitot device 120.

Consequently, in the structure in which the seal 91 that holds the airtightness between the pitot device 120 and the window 16 is pressed by the retainer 92, a mechanism for avoiding load transmission between the pitot device 120 and the window 16 can be achieved by the configuration in which the seal 91 is fixed to only one of the pitot device 120 and the window 16, and slidably supported by the other of the pitot device 120 and the window 16. Because of the mechanism, the airtightness at a position where it is difficult to hold the airtightness due to relative displacement of objects to be sealed (the pitot device 120 and the window 16) caused when the bracket body 125 is deformed by the load from the pitot device 120 by the aerodynamic load can be reliably held by the seal 91.

In the present embodiment, the pitot device 120 and the pitot bracket 124 integrated with the pitot device 120 constitute a penetration member penetrating the airframe. However, the pitot bracket 124 is not always required depending on forms of the pitot device 120 and the window substitute member 8. Therefore, a portion of the pitot device 120 may be configured to penetrate the airframe.

The constitutions described in the aforementioned embodiments may be also freely selected or changed into other constitutions without departing from the gist of the present invention.

In a case in which there exists a window or a door having a size fitted to a size of the arm 30 of the first embodiment or the pitot bracket 124 of the second embodiment, the arm 30 or the pitot bracket 124 may be passed through an opening of the window or the door itself. In this case, it is not necessary to use a substitute member for the window or the door. A gap between a peripheral edge portion of the opening of the window or the door and an outer peripheral portion of the arm 30 or the pitot bracket 124 may be sealed by a seal, and the seal may be pressed by a retainer.

Even when the substitute member for the window or the door is not used, it is possible to easily attach the penetration member to the airframe since the structural members extending longitudinally and laterally on the inner side of the skin are not lost when the window or the door that is an opening previously formed in the skin is used. It is also easy to restore the airframe after removing the penetration member.

What is claimed is:
1. An aircraft comprising:
   a penetration member that penetrates an airframe between an inside and an outside via an opening provided in the airframe, a part of the penetration member protruding outside the airframe;
   a seal that seals a gap set between an opening formation member forming the opening and the penetration member; and
   a retainer that presses the seal against the penetration member and the opening formation member,
   wherein each of the penetration member and the opening formation member includes a receiving section that receives the seal, both of the receiving sections are arranged along a direction connecting one side and the other side of the gap with the gap therebetween, and the seal is fixed to only one of the receiving section of the penetration member and the receiving section of the opening formation member.

2. The aircraft according to claim 1,
wherein the opening formation member is a window substitute member that is provided in a window frame of a window provided in the airframe instead of an original window panel.

3. The aircraft according to claim 1,
wherein the opening formation member includes
a support that rises from a peripheral edge portion of the formed opening toward an airframe inner side along a penetration direction in which the penetration member penetrates the airframe, and
a flange as the receiving section that is provided on the support, and
the flange of the opening formation member and the receiving section of the penetration member are arranged along a direction perpendicular to or substantially perpendicular to the penetration direction with the gap therebetween.

4. The aircraft according to claim 1,
wherein the opening formation member includes a peripheral wall that rises from a peripheral edge portion of the formed opening toward an airframe inner side along a penetration direction in which the penetration member penetrates the airframe,
the penetration member includes an annular portion that is arranged with the gap between the annular portion and a distal end of the peripheral wall, and
an outer peripheral portion of the peripheral wall as the receiving section of the opening formation member and an outer peripheral portion of the annular portion as the receiving section of the penetration member are arranged along the penetration direction.

5. The aircraft according to claim 1,
wherein the penetration member includes
a first portion that is located outside the airframe, and
a second portion that is located inside the airframe, and
a detection device that detects a physical quantity is provided at the first portion.

6. The aircraft according to claim 5,
wherein the detection device detects a physical quantity with regard to a water droplet included in an atmosphere outside the airframe.

7. The aircraft according to claim 5,
wherein the detection device detects at least a total pressure out of the total pressure and a static pressure.

8. The aircraft according to claim 5,
wherein the second portion of the penetration member is coupled to a support device provided inside the airframe.

9. The aircraft according to claim 8,
wherein the support device comprises a plurality of seat rails that support seats within a cabin, and
a mount that is provided on the seat rails.

10. The aircraft according to claim 9,
wherein the seat rails are installed on a floor of the cabin.

11. The aircraft according to claim 5,
wherein the detection device is a pitot device.

12. The aircraft according to claim 1,
wherein the penetration member includes
a detection device that detects a physical quantity outside the airframe, and
a member that is integrated with the device.

13. The aircraft according to claim 12,
wherein the detection device is a pitot device.

14. The aircraft according to claim 12,
wherein the detection device detects a physical quantity with regard to a water droplet included in an atmosphere outside the airframe.

15. The aircraft according to claim 1,
wherein the penetration member is a portion of a detection device that detects a physical quantity outside the airframe.

16. The aircraft according to claim 1,
wherein one end side of the seal is fixed to the receiving section of the penetration member, and
another end side of the seal is simply supported by the receiving section of the opening formation member.

17. An aircraft comprising:
a penetration member that penetrates an airframe between an inside and an outside via an opening provided in the airframe;
a seal that seals a gap set between an opening formation member forming the opening and the penetration member; and
a retainer that presses the seal against the penetration member and the opening formation member,
wherein each of the penetration member and the opening formation member includes a receiving section that receives the seal,
both of the receiving sections are arranged along a direction connecting one side and the other side of the gap with the gap therebetween,
the seal is fixed to only one of the receiving section of the penetration member and the receiving section of the opening formation member,
one end side of the seal is fixed to the receiving section of the penetration member,
another end side of the seal is simply supported by the receiving section of the opening formation member, and
the another end side of the seal is slidably supported by the receiving section of the opening formation member.

18. A railway vehicle comprising:
a penetration member that penetrates a structure body of the railway vehicle between an inside and an outside via an opening provided in the structure body, a part of the penetration member protruding outside the structure body;
a seal that seals a gap set between an opening formation member forming the opening and the penetration member; and
a retainer that presses the seal against the penetration member and the opening formation member,
wherein each of the penetration member and the opening formation member includes a receiving section that receives the seal,
both of the receiving sections are arranged along a direction connecting one side and the other side of the gap with the gap therebetween, and
the seal is fixed to only one of the receiving section of the penetration member and the receiving section of the opening formation member.

19. The railway vehicle according to claim 18,
wherein the penetration member includes a detection device that detects a physical quantity with regard to a water droplet included in an atmosphere outside the structure body.

20. The railway vehicle according to claim 18,
wherein the railway vehicle is a superconducting magnetic levitation linear motor car.

* * * * *